United States Patent [19]

Cornils et al.

[11] Patent Number: 4,472,526
[45] Date of Patent: Sep. 18, 1984

[54] PROCESS FOR PRODUCING ETHANOL AND N-PROPANOL FROM METHANOL AND SYNTHESIS GAS

[75] Inventors: Boy Cornils, Dinslaken; Carl-Dieter Frohning, Oberhausen; Helmut Bahrmann, Hünxe; Wolfgang Lipps, Oberhausen, all of Fed. Rep. of Germany

[73] Assignee: Ruhrchemie Aktiengesellschaft, Oberhausen, Fed. Rep. of Germany

[21] Appl. No.: 427,092

[22] Filed: Sep. 29, 1982

[30] Foreign Application Priority Data

Jan. 21, 1982 [DE] Fed. Rep. of Germany ....... 3201665

[51] Int. Cl.$^3$ .............................................. B01J 31/24
[52] U.S. Cl. .................................... 502/162; 502/161; 568/902
[58] Field of Search ........... 252/429 R, 431 C, 431 P; 502/162, 161

[56] References Cited

U.S. PATENT DOCUMENTS

| | | | |
|---|---|---|---|
| 3,635,937 | 1/1972 | Bauer et al. | 252/431 P X |
| 3,636,091 | 1/1972 | Mason et al. | 252/431 P X |
| 4,142,060 | 2/1979 | Kuntz | 252/431 P X |
| 4,253,987 | 3/1981 | Fiato | 252/429 R |
| 4,315,867 | 2/1982 | Hanssle | 252/431 P X |
| 4,366,259 | 12/1982 | Knifton et al. | 252/431 P X |

*Primary Examiner*—Patrick Garvin
*Attorney, Agent, or Firm*—Jordan B. Bierman; Linda Bierman

[57] ABSTRACT

The present invention relates to a process for producing ethanol and n-propanol by reacting methanol with carbon monoxide and hydrogen at elevated pressure and temperature. A system consisting of a cobalt compound, a ruthenium compound, an iodide, and an organic phosphine serves as the catalyst. The organic phosphine contains a group having a $-SO_3M$, $-COOM$ or $-OSO_3M$ radical.

7 Claims, No Drawings

PROCESS FOR PRODUCING ETHANOL AND N-PROPANOL FROM METHANOL AND SYNTHESIS GAS

This application claims the priority of German application No. P 32 01 665.4, filed Jan. 21, 1982.

The invention relates to a process for producing ethanol and n-propanol from methanol and synthesis gas, i.e. a mixture of carbon monoxide and hydrogen, in the presence of cobalt and ruthenium as catalysts. This reaction, which is termed homologization, enables higher homologous alcohols to be produced from methanol by introducing one or more $CH_2$ groups.

Homologization is attracting increasing interest since it provides a means of obtaining higher alcohols which does not depend on the use of petroleum. Synthesis gas or methanol produced therefrom is required as feedstock. Synthesis gas can be obtained by various technically feasible processes, e.g. from coal or natural gas.

Conversion of methanol into ethanol with hydrogen and carbon monoxide at elevated temperatures and pressures and in the presence of a cobalt catalyst is known (see e.g. DE-PS No. 867 849). The reaction proceeds according to the following reaction equation:

$$CH_3OH + CO + 2H_2 \rightarrow C_2H_5OH + H_2O$$

wherein higher alcohols can be formed in a minor amount corresponding to the equation:

$$CH_3OH + n(CO + 2H_2) \rightarrow CH_3(CH_2)_nOH + n\, H_2O.$$

Originally cobalt was used exclusively as the catalyst for the reaction; however, over the course of time, multicomponent catalysts have become increasingly important.

EP-OS No. 22,038 describes the production of ethanol from methanol using a catalyst of cobalt together with organic and inorganic iodine compounds, and ammonium or phosphonium compounds, as well as a ruthenium compound as promoters. Ethanol and acetaldehyde are produced simultaneously when a catalyst system consisting of a cobalt, an iodine and bidentate phosphine component as described in EP-OS 10,373 are used. The selectivity with regard to ethanol is said to be increased by adding an inert solvent. Ruthenium is mentioned as an additional optional component of the catalyst.

According to U.S. Pat. No. 4,133,966, ethanol is produced from synthesis gas and methanol using a catalyst consisting of a cobalt acetylacetonate, an organic compound of an element of Group VA of the Periodic Table, a ruthenium compound, and an iodine compound. Similarly, British Pat. No. 2,036,739 teaches a catalyst consisting of cobalt, ruthenium or osmium, a halogen, and an organic compound of an element of Group VA of the Periodic Table as being useful in the production of ethanol from methanol and synthesis gas.

Also U.S. Pat. No. 4,233,466 teaches the use of cobalt, ruthenium iodine and a tertiary phosphine as catalyst components in the synthesis of ethanol from methanol and synthesis gas; however, maintaining ratios of individual components within certain limits results in a stabilizing effect and increases the activity of the catalyst system. U.S. Pat. Spec. No. 4,239,924 describes a catalyst system for producing ethanol from methanol consisting of dimeric cobalt tricarbonyl ligand complex, whose ligand consists of a compound of an element of Group VA of the Periodic Table and also contains iodine and ruthenium acetylacetonate as promoters.

A process for homologization of methanol with synthesis gas in the presence of an inert solvent and a catalyst system is described by EP-OS No. 30,434. This system comprises defined cobalt-ruthenium phosphines or phosphites. Soluble Ru complexes together with $Co_2(CO)_{8-n}(PR_3)_n$ complexes may be used instead of the defined cobalt-ruthenium complexes.

Despite the above procedures, the reaction yields obtained are insufficient for industrial use. Furthermore, numerous, different individual compounds occur as undesired by-products in large amountss. Therefore, in addition to the desired alcohols, methane, ethane, and propane, various ethers as well as methyl acetate, ethyl acetate, propyl acetate, acetaldehyde-dimethyl-acetal, acetaldehyde-methyl-ethylacetal and acetaldehyde-diethyl-acetal as well as other compounds are produced. The industrial process is therefore expensive as it is necessary to isolate, e.g. by hydrogenation, saponification and distillation, the useful product fractions from the by-products.

One method of improving the selectivity of the conversion is to add a solvent to the reactants. However, this reduces the conversion rate considerably for a given reactor volume and time. Therefore, with known processes, methanol homologization can be carried out with satisfactory selectivity and low conversion rates, or with high conversion rates and low selectivity.

Hence, an object of the invention is to develop a procedure whereby methanol can be converted into ethanol and n-propanol with both a high degree of selectivity and a high conversion rate. A second object is to substantially reduce the number of the by-products of the homologization reaction, so that the desired products can be separated in a simple manner.

The invention achieves these objectives by a process for producing ethanol and n-propanol which includes reacting methanol with carbon monoxide and hydrogen at elevated pressures of 200 to 600 bars and temperatures of 150° to 250° C. in the presence of a catalyst which contains a cobalt compound, a ruthenium compound, an iodide and an organic phosphine. The invention is characterized in that the organic phosphine contains a group having a $-SO_3M$, $-OSO_3M$ or $-COOM$ group; wherein M denotes H, alkali metals or ammonium. Preferably, the $CO:H_2$ volume ratio is 1:2.0 to 1:3.5; the molar ratio of cobalt to methanol is 1:30 to 1:5000; molar ratio of cobalt to iodine is 1:0.1 to 1:2; the molar ratio of cobalt to ruthenium is 1:0.01 to 1:0.05, and the molar ratio of cobalt to phosphorus is 1:0.05 to 1:2.5.

Surprisingly, it was found that a considerable improvement in the conversion rate of methanol and the selectivity as to ethanol and n-propanol in the homologization is achieved by using such phosphines. As compared with the same process with triphenyl phosphines containing no $-SO_3M$, $-OSO_3M$ or $-COOM$ group, it is found that (Comparision Example 7) conversion rates and selectivities which are considerably improved can be achieved with the present invention (see Examples 1 to 6).

Organic phosphines which can be used within the scope of the present invention are compounds having the general formulae $$R_1R_2P\,[(CH\,R_3)_m-COOH] \quad\quad I$$

or

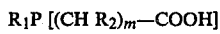   II wherein m is an integar from 1 to 6, and $R_1$, and $R_3$ individually denote hydrogen, straight-chain or branched (also bicyclic) alkyl radicals with 1 to 16 carbon atoms, or aryl radicals with 6 to 15 carbon atoms. In the case of (I), $R_1$ and $R_2$ may be joined to one another in pairs to form a phosphorus-containing cyclic or bicylic system.

Examples of useful alkyl radicals are methyl, ethyl, propyl, butyl, pentyl, i-propyl, i-hexadecyl, neopentyl. Cycloalkyl radicals operable herein are cyclohexyl, dicyclopentyl, tricyclo(5,2,1,0$^{2,6}$)decenyl, and aryl radicals which may be used are phenyl, tolyl, naphthyl, phthalyl.

Examples of alkyl radicals joined to one another are

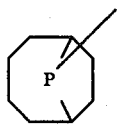 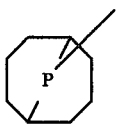

(9)-phosphabicyclo-(4,2,1)nonane    (9)-phosphabicyclo-(3,3,1)nonane

Examples of compounds corresponding to the described formulae and which can be used within the scope of the procedure according to the invention are:
(1) bis-(tricyclo-(5,2,1,0$^{2,6}$)decenyl)-2-carboxyethyl-phosphine,
(2) 2-carboxyethyl-dicyclohexylphosphine,
(3) bis-(2-carboxyethyl)-cyclohexyl-phosphine, and
(4) a mixture of 9-(2-carboxyethyl)-9-phosphabicyclo-(4,2,1)nonane and 9-(2-carboxyethyl)-9-phosphabicyclo(3,3,1)nonane.

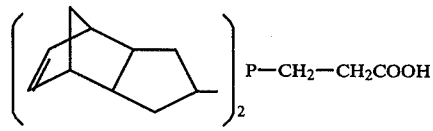 (1)

 (2)

 (3)

(4)
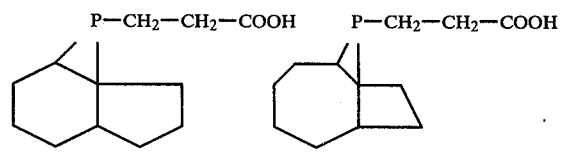

[3,3,1]         [4,2,1]

Further suitable phosphines that can be used within the scope of the procedure according to the invention are:
(5) the trisodium salt of (2-sulphatopropyl)-bis(m-sulphophenyl)- phosphine and
(6) (bis-1,3-(m-sulphophenyl)phenyl-phosphino)propane

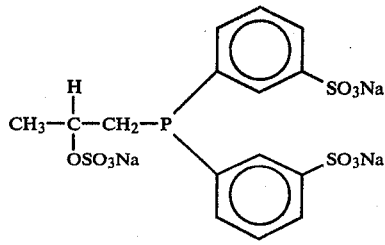

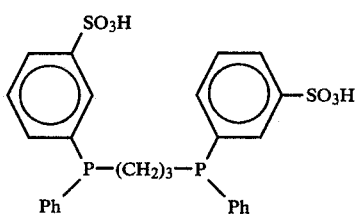

The above-mentioned phosphorus compounds with —COOM groups can be obtained by radical addition of a P—H bond to a C—C double bond (see e.g. DE-OS No. 29 39 588 and J. Org. Chem., 26 (1961) 138). Compounds 1 to 4 are obtained by reacting the corresponding mono- and ditertiary phosphines with acrylic acid. In the case of monotertiary phosphines, two acrylic acid radicals add on (cf. compound 3). The trisodium salt of (2-sulphato-propyl)-bis(m-sulphophenyl)phosphine (Compound 5) and [bis-1,3-(m-sulphophenyl)phenyl-phosphino]propane (Compound 6) are obtained by sulphonation of allyl diphenyl phosphine and 1,3-diphenyl-phosphinopropane.

These phosphorus compounds, together with the cobalt and ruthenium compounds, under the reaction conditions form complex compounds which may also contain halogen, carbon monoxide and hydrogen. These compounds constitute part of the effective catalyst system.

Cobalt is added to the reaction mixture generally in the form of a salt such as cobalt-2-ethylhexanoate, cobalt acetylacetonate, a cobalt halide, cobalt nitrate, or as an oxide or hydroxide. Cobalt carbonate has proved particularly suitable. It is however also possible to use metallic cobalt in finely divided form. An important factor is for the cobalt or the cobalt compound to react with carbon monoxide and hydrogen with the formation of a cobalt carbonyl or hydrocarbonyl.

A further constituent of the catalyst system corresponding to the new process is ruthenium, which is added to the reaction mixture as a compound, e.g. a ruthenium halide, ruthenium 2-ethylhexanoate, ruthenium chloride, (NH$_4$)$_4$(Ru$_2$OCl$_{10}$), preferably as ruthenium acetylacetonate, which is converted under the reaction conditions into the corresponding carbonyl complex.

Finally, the catalyst system also contains iodine in ionic form. Alkali metal salts and, particularly advantageously, cobalt iodide may be used as iodine salts.

The catalyst system used according to the invention may be added to the reaction mixture in the form of its individual constituents. Pre-formulation of the metal complex compounds which are the components of the catalyst system is unnecessary; however, a preformed catalyst may be used if so desired. The catalyst system can be used repeatedly.

The methanol employed as starting material can be used in the form of the technical product, with a water content of 4 to 6%. Additional purification is unnecessary. The reaction mixture employed at the beginning contains 5 to 25% by weight of water based on methanol. The conversion is increased by the addition of the water. Larger amounts of water affect the conversion only slightly, while smaller amounts produce no or only insignificant increases in conversion. The water is conveniently added together with the methanol to the reactor.

The molar ratio of cobalt to methanol is 1:30 to 1:5000. Cobalt and phosphine are used in a molar ratio of 1:0.5 to 1:2.5. The atomic ratio of cobalt to ruthenium is 1:0.01 to 1:0.05. Cobalt and iodine are employed in a molar ratio of 1:0.1 to 1:2.

The carbon monoxide/hydrogen mixture should not contain any impurities such as sulphur which affect the activity of the catlyst system. Carbon dioxide, inert hydrocarbons and/or nitrogen up to 5% by volume referred to the total mixture do not have an adverse effect.

The new process can be carried out batchwise and also continuously. In general, the conversion of methanol, carbon monoxide, and hydrogen takes place at temperatures of 150° to 250° C., in particular 160° to 230° C. The pressure is maintained at values between 200 to 600 bars, preferably 450 to 600 bars. The molar ratio of hydrogen to carbon monoxide in the synthesis gas is 1:2.0 to 1:3.5.

The following Examples illustrate the invention.

The selectivities given in the Tables were calculated according to the following equation:

$$\text{Selectivity with regard to product } i: (\%) = \frac{\text{Number of mols of product } i \times 100}{\text{Total number of mols of all the products}}$$

EXAMPLE 1

9.375 mols (300 g) methanol, 1.67 mols (30 g) water, 25.22 mmols (3 g CoCO$_3$) Co, 10 mmols (1.5 g NaI) iodide and 30.56 mmols (11.2 g) bis-(tricyclo(5,2,1,0$^{2,6}$)decenyl)-2-carboxyethylphosphine and 0.83 mmol (0.33 g Ru(III)acetylacetonate) Ru are placed in a steel autoclave (1 liter capacity) provided with a stirrer, thermometer, sampling tube and a gas collector serving to trap gaseous constituents. A pressure of 550 bars is then established with synthesis gas, the autoclave is heated to 200° C., and the reaction is continued for 3 hours while forcing in synthesis gas under pressure.

After cooling the reaction mixture and releasing the pressure into the gas collector, as average sample is obtained whose gas chromatographic composition is given in the Table.

EXAMPLES 2–4

These Examples are carried out similarly to Example 1, the following phosphine-containing components being used:

| Example 2: | 27.74 mmols (7.2 g) 2-carboxyethyl dicyclohexylphosphine |
|---|---|
| Example 3: | 24.33 mmols (6.3 g) bis-(2-carboxyethyl)-cyclohexylphosphine |
| Example 4: | 27.73 mmols (6.6. g) of a mixture of 9-(2-carboxyethyl)-9-phosphabicyclo(4,2,1) nonane, and 9-(2-carboxyethyl)-9-phosphabicyclo(3,3,1) nonane |

The gas chromatographic composition of the individual reaction products is given in Table 1.

EXAMPLE 5

9.375 mols (330 g) methanol, 1.67 mols (30 g) water, 12.61 mmols (1.5 g CoCO$_3$) Co, 12.68 mmols (1.9 g) sodium iodide, 0.43 mmol (0.17 g Ru(acac)$_3$)* Ru, as well as 27.8 mmols (15.3 g) of the trisodium salt of (2-sulphatopropyl)bis-(m- sulphophenyl)phosphine are placed in the steel autoclave of the apparatus according to Example 1. A pressure of 550 bars is established with synthesis gas (CO/H$_2$=1:3), the autoclave is heated to 200° C., and the reaction is continued for 3 hours while forcing in synthesis gas under pressure. After cooling the mixture and releasing the pressure into the gas collector, an average sample is taken whose gas chromatographic composition is given in Table 1.

\* acac=acetylacetonate.

EXAMPLE 6

The process is carried out similarly to Example 5, 13.99 mmols (8.0 g) of (bis-1,3-(m-sulphophenyl)-phenylphosphino) propane being used as the phosphine component.

COMPARISON EXAMPLE 7

14.1 mmols (3.7 g) of triphenylphosphine are used as the phosphine component under the same conditions as in Example 5.

The experimental results of all the described Examples are set forth in Tables 1 and 2.

TABLE 1

| | GLC analysis (% by weight) | | | | | | |
|---|---|---|---|---|---|---|---|
| Experiment No. | 1 | 2 | 3 | 4 | 5 | 6 | 7 |
| Methanol | 43,3 | 64,9 | 43,1 | 33,0 | 83,2 | 45,7 | 85,5 |
| Ethanol | 38,4 | 29,0 | 45,4 | 51,3 | 12,9 | 45,6 | 10,2 |
| n-propanol | 1,5 | 1,2 | 3,8 | 4,9 | 0,2 | 2,0 | 0,1 |
| Hydrocarbon | 2,9 | 1,6 | 0,3 | 1,3 | 0,4 | 1,7 | 0,2 |
| Acetaldehyde | — | — | 0,2 | 0,2 | — | — | 0,2 |
| Ethers | 12,1 | 1,5 | 1,1 | 3,2 | 0,7 | 2,6 | 0,5 |
| Esters | 1,0 | 0,9 | 1,8 | 3,0 | 0,4 | 1,2 | 0,6 |
| Acetals | — | 0,4 | 1,5 | 1,0 | 1,8 | — | 1,9 |
| C$_4$-C$_6$-ols | 0,4 | 0,4 | 2,3 | 1,7 | 0,3 | 1,0 | 0,6 |
| Remainder, second runnings | 0,3 | 0,1 | 0,5 | 0,4 | 0,1 | 0,2 | 0,2 |

TABLE 2

| | Conversions and selectivities | | | | | | |
|---|---|---|---|---|---|---|---|
| Example | 1 | 2 | 3 | 4 | 5 | 6 | 7 |
| Conversion (%) | 56 | 39 | 62 | 62 | 15 | 59 | 15 |
| Selectivities (%) | | | | | | | |
| Ethanol | 69 | 78 | 81 | 80 | 78 | 80 | 62 |
| n-propanol | 2 | 3 | 5 | 6 | 1 | 3 | — |
| Hydrocarbon | 9 | 13 | 6 | 6 | 9 | 10 | 6 |
| Acetaldehyde | — | — | — | — | — | — | 1 |
| Ethers | 17 | 3 | 2 | 4 | 4 | 4 | 5 |
| Esters | 2 | 2 | 2 | 2 | 2 | 1 | 3 |
| Acetals | — | — | 1 | 1 | 5 | — | 21 |
| Higher alcohols | 1 | 1 | 2 | 1 | 1 | 1 | 1 |
| Remainder | — | — | 1 | — | — | 1 | 1 |

We claim:

1. In a catalyst for producing ethanol and n-propanol from methanol, carbon monoxide and hydrogen, said catalyst containing a cobalt compound, a ruthenium compound, an iodide, and an organic phosphine, the improvement wherein the orgnic phosphine has a functional group selected from the class consisting of —SO$_3$M, —COOM and —OSO$_3$M wherein M is hydrogen, alkali metals, or ammonium.

2. The catalyst of claim 1 wherein said cobalt and said iodide are present in a molar ratio of about 1:0.1 to about 1:2.

3. The catalyst of claim 1 wherein said cobalt and said ruthenium are present in a molar ratio of about 1:0.01 to about 1:0.05.

4. The catalyst of claim 1 wherein said cobalt and said phosphine are present in a molar ratio of about 1:0.5 to about 1:2.5.

5. The catalyst of claim 1 wherein said phosphine is at least one substance selected from the group consisting of $$R_1R_2P[(CHR_3)_m\text{—COOH}] \qquad \text{I}$$

$$R_1P[(CHR_2)_m\text{—COOH}]_2 \qquad \text{II}$$

wherein m is an integer from 2–6 and $R_1$, $R_2$ and $R_3$ are individually selected from the group consisting of hydrogen, straight and branched alkyls with 1–16 carbon atoms, and aryls with 6–15 carbon atoms.

6. The catalyst of claim 5 wherein said phosphines of formula I have $R_1$ and $R_2$ connected to form a cyclic or bicyclic system.

7. The catalyst of claim 1 wherein said phosphine is selected from the group consisting of
bis-tricyclo(5,2,1,0$^{2,6}$)decenyl)-2-carboxyethylphosphine,
2-carboxyethyl-dicyclohexylphosphine,
bis-(2-carboxyethyl)-cyclohexyl-phosphine,
(2-sulphatopropyl)-bis(m-sulphophenyl)phosphine-trisodium salt,
(bis-1,3-(m-sulphophenyl(phenylphosphino)propane trisodium salt,
9-(2-carboxyethyl)-9-phosphabicyclo(4,2,1)nonane,
9-(2-carboxyethyl)-9-phosphabicyclo-(3,3,1)nonane,
and mixtures thereof.

* * * * *